US010624600B2

(12) United States Patent
Park et al.

(10) Patent No.: US 10,624,600 B2
(45) Date of Patent: *Apr. 21, 2020

(54) METHOD AND APPARATUS FOR MANAGING X-RAY ACCUMULATION AMOUNT

(71) Applicant: SAMSUNG ELECTRONICS CO., LTD., Suwon-si (KR)

(72) Inventors: Jun-young Park, Suwon-si (KR); Se-won Kim, Suwon-si (KR); Yeon-ju Lee, Suwon-si (KR); Byung-sun Choi, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 300 days.

This patent is subject to a terminal disclaimer.

(21) Appl. No.: 15/600,391

(22) Filed: May 19, 2017

(65) Prior Publication Data
US 2017/0251993 A1 Sep. 7, 2017

Related U.S. Application Data

(63) Continuation of application No. 14/470,285, filed on Aug. 27, 2014, now Pat. No. 9,681,850.

(30) Foreign Application Priority Data

Aug. 27, 2013 (KR) .................. 10-2013-0102016

(51) Int. Cl.
A61B 6/00 (2006.01)
G06F 19/00 (2018.01)
G16H 10/60 (2018.01)

(52) U.S. Cl.
CPC ............. A61B 6/542 (2013.01); A61B 6/463 (2013.01); A61B 6/563 (2013.01); G06F 19/3481 (2013.01); G16H 10/60 (2018.01)

(58) Field of Classification Search
CPC ......... A61B 6/542; A61B 6/463; A61B 6/563; G06F 19/3481; G06F 19/322
See application file for complete search history.

(56) References Cited

U.S. PATENT DOCUMENTS 7,254,623 B1 * 8/2007 Toth .................. A61B 6/032
707/999.005
8,788,292 B2 7/2014 Bourdeaux et al.
(Continued)

FOREIGN PATENT DOCUMENTS

EP 1806162 A2 7/2007
EP 2293654 A2 3/2011
(Continued)

OTHER PUBLICATIONS

Communication dated Aug. 5, 2015, issued by the Korean Intellectual Property Office in counterpart Korean Application No. 2013-0102016.
(Continued)

Primary Examiner — Courtney D Thomas
(74) Attorney, Agent, or Firm — Sughrue Mion, PLLC

(57) ABSTRACT

An X-ray imaging method includes obtaining first information including X-ray accumulation amount of an object; determining an imaging protocol for imaging the object based on the received first information; and acquiring an X-ray image of the object based on the determined imaging protocol. The first information including the X-ray accumulation amount of the object is obtained from a device of the object via a short range wireless communication or from an external database based on authentication information input received from the object.

17 Claims, 14 Drawing Sheets

(56) References Cited

U.S. PATENT DOCUMENTS

| | | | |
|---|---|---|---|
| 9,681,850 B2* | 6/2017 | Park | A61B 6/542 |
| 2005/0121505 A1 | 6/2005 | Metz et al. | |
| 2007/0232868 A1 | 10/2007 | Reiner | |
| 2012/0106817 A1 | 5/2012 | Shih et al. | |
| 2012/0189098 A1* | 7/2012 | Liu | A61B 6/4283 378/62 |
| 2012/0232929 A1 | 9/2012 | Experton | |
| 2012/0245466 A1 | 9/2012 | Ganguly | |

FOREIGN PATENT DOCUMENTS

| | | |
|---|---|---|
| JP | 2007097909 A | 4/2007 |
| JP | 2008284294 A | 11/2008 |
| JP | 2009172138 A | 8/2009 |
| JP | 2010221032 A | 10/2010 |
| KR | 1020130094457 A | 8/2013 |
| WO | 2008/111355 A1 | 9/2008 |

OTHER PUBLICATIONS

Communication dated Feb. 3, 2015, issued by the European Patent Office in counterpart European Application No. 14182410.2.

Communication dated May 21, 2015, issued by the Korean Intellectual Property Office in counterpart Korean Application No. 2013-0102016.

Communication dated Nov. 25, 2014, issued by the Korean Intellectual Property Office in counterpart Korean Application No. 10-2013-0102016.

Communication dated Nov. 26, 2014, issued by the International Searching Authority in counterpart International Application No. PCT/KR2014/007955.

Communication dated Nov. 4, 2015, issued by the Korean Intellectual Property Office in counterpart Korean Application No. 10-2015-0125601.

* cited by examiner

FIG. 2

```
START
  ↓
OBTAIN INFORMATION OF X-RAY
ACCUMULATION AMOUNT OF OBJECT        — S210
  ↓
DETERMINE IMAGING PROTOCOL BASED ON
X-RAY ACCUMULATION AMOUNT OF OBJECT  — S220
  ↓
OBTAIN X-RAY IMAGE OF OBJECT
BASED ON DETERMINED IMAGING PROTOCOL — S230
  ↓
END
```

FIG. 3

| | Item | Value |
|---|---|---|
| 310 | Object ID | mcJeong |
| 312 | Object Name | Jeong Min Cheol |
| 314 | Age | 33 Years |
| 316 | Gender | Male |
| 318 | Weight | 77kg |
| 320 | Overall Accumulated X-ray Dose | 15mV |
| 322 | Head Accumulated X-ray Dose | 9mV |
| 324 | Chest Accumulated X-ray Dose | 3mV |
| 326 | Abdomen Accumulated X-ray Dose | 3mV |
| 328 | Last X-ray Dose date | 2013/08/17 |

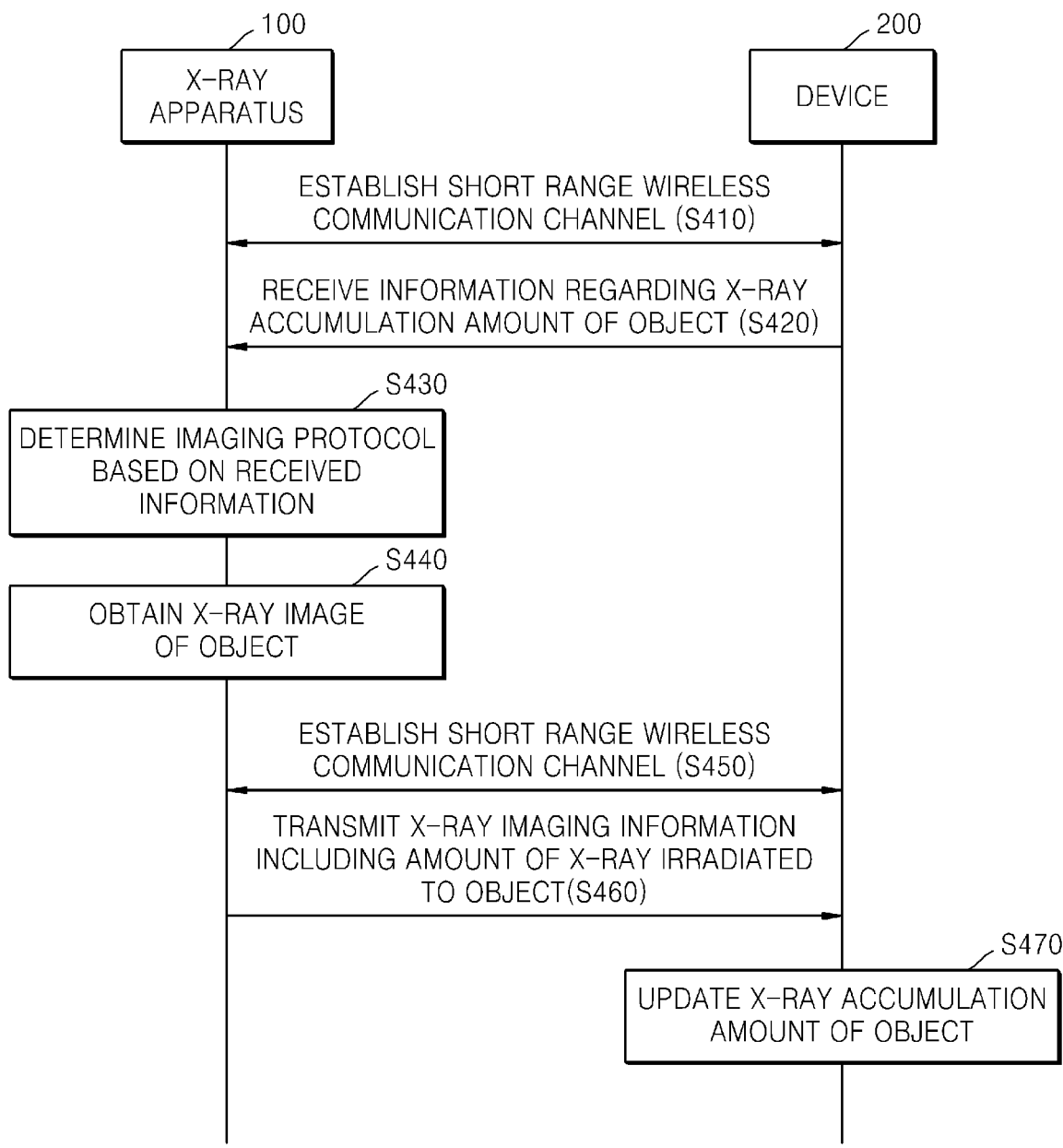

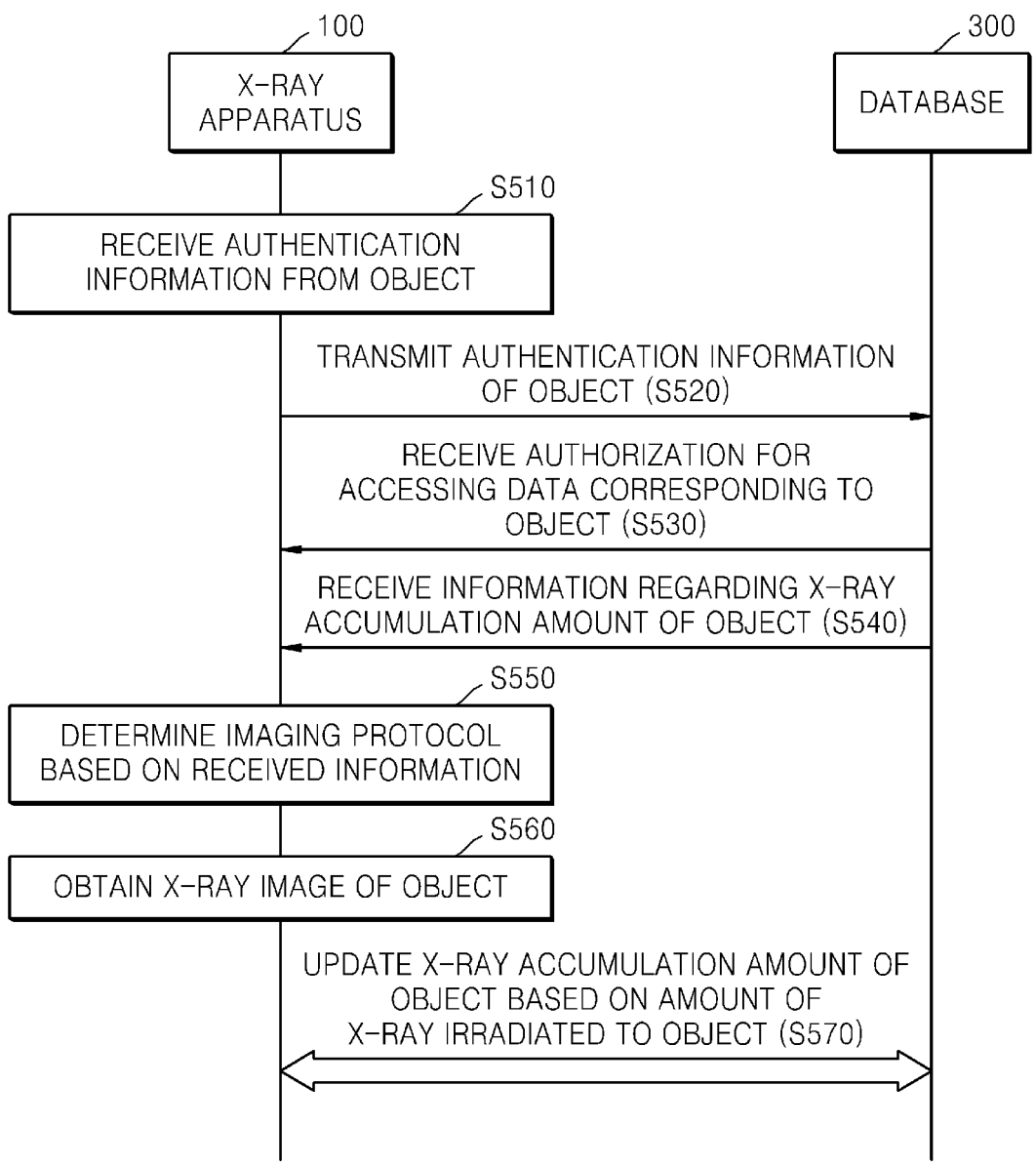

FIG. 6

| Item | Value |
|---|---|
| Object ID | mcJeong |
| Object Name | Jeong Min Cheol |
| X-ray Dose Amount | 0.5mV |
| Region | Head |
| Date | 2013/08/17 |

310 — Object ID
312 — Object Name
614 — X-ray Dose Amount
616 — Region
618 — Date

FIG. 7

START
↓
TRANSMIT INFORMATION REGARDING X-RAY ACCUMULATION AMOUNT OF OBJECT TO X-RAY APPARATUS — S710
↓
RECEIVE X-RAY IMAGING INFORMATION INCLUDING AMOUNT OF X-RAY IRRADIATED TO OBJECT FROM X-RAY APPARATUS — S720
↓
UPDATE X-RAY ACCUMULATION AMOUNT OF OBJECT — S730
↓
END

METHOD AND APPARATUS FOR MANAGING X-RAY ACCUMULATION AMOUNT

CROSS-REFERENCE TO RELATED APPLICATION

This application is a continuation of U.S. application Ser. No. 14/470,285 filed on Aug. 27, 2014, which claims priority from Korean Patent Application No. 10-2013-0102016, filed on Aug. 27, 2013, in the Korean Intellectual Property Office, the disclosures of which are incorporated herein in their entirety by reference.

BACKGROUND

1. Field

Apparatuses and methods consistent with exemplary embodiments relate to managing X-ray accumulation amounts with respect to an object.

2. Description of the Related Art

X-ray apparatuses including an X-ray imaging device and a computed tomography (CT) imaging device irradiate an X-ray, which is a type of radiation having a short wavelength and high penetrability.

However, excessive X-ray exposure may cause damage to cellular tissue of an object. Therefore, it is important to properly manage X-ray accumulation amounts.

Currently, a patient may be informed about amount of X-ray irradiated to him/her in a single X-ray imaging. However, due to medical security problems or difficulty of system integration, it is difficult to manage information of X-ray radiation amounts of hospitals in a single system.

Therefore, it is difficult for a patient to know total amount of the received X-ray radiation. Furthermore, when a radiological technologist performs an X-ray imaging, the radiological technologist determines an imaging protocol without consideration of a total X-ray accumulation of an object and, thus, excessive amount of X-ray may be irradiated to the object.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide a method and an apparatus for performing an X-ray imaging operation of an object based on X-ray accumulation amount of the object and a method and an apparatus for managing X-ray accumulation amounts with respect to an object.

According to an exemplary embodiment, there is provided an X-ray imaging method including obtaining information of X-ray accumulation amount of an object; determining an imaging protocol for imaging the object based on the information of X-ray accumulation amount of the object; and obtaining an X-ray image of the object based on the determined imaging protocol, wherein the information of X-ray accumulation amount of the object is obtained from a device of the object via a designated short range wireless communication method or obtained from an external database based on authentication information input by the object.

The X-ray imaging method may further include obtaining second information regarding the object, wherein the determining the imaging protocol includes determining the imaging protocol in further consideration of the second information.

The second information may include identification (ID) information of the object, the first information may include X-ray accumulation amounts for respective portions of the object, and the determining the imaging protocol may include determining an imaging portion of the object based on the ID information of the object; and determining the imaging protocol based on the determined imaging portion, the X-ray accumulation amount included into the first information and corresponding to the determined imaging portion, and an X-ray tolerance for the determined imaging portion.

The first information may include X-ray accumulation amounts for respective portions of the object.

The X-ray imaging method may further include transmitting, to the device of the object, X-ray imaging information including an overall amount of an X-ray radiation irradiated to the object according to the determined imaging protocol, via the short range wireless communication.

The X-ray imaging information may further include information of at least one of imaged portions of the object and amounts of the X-ray radiation irradiated to respective imaged portions of the object.

The X-ray imaging information may further include information regarding at least one of a technologist who performed the imaging, a doctor who ordered the imaging, an imaging date, an imaging time, an X-ray image obtained via the determined imaging protocol, and a result of diagnosis based on the X-ray image.

The obtaining the first information may include receiving the X-ray accumulation amount of the object from the device of the object via a near field communication (NFC) as the device of the object is tagged to an X-ray apparatus which performs the X-ray imaging.

The short range wireless communication may include at least one of a near field communication (NFC), Bluetooth, and Wi-Fi.

According to another exemplary embodiment, there is provided an X-ray apparatus including an accumulation information obtainer for obtaining information of X-ray accumulation amount of an object; an imaging protocol determiner for determining an imaging protocol for imaging the object based on the information of X-ray accumulation amount of the object; and a scanner for obtaining an X-ray image of the object based on the determined imaging protocol, wherein the information of X-ray accumulation amount of the object is obtained from a device of the object via a designated short range wireless communication method or obtained from an external database based on authentication information input by the object.

The accumulation information obtainer may obtain second information of the object, and the imaging protocol determiner may determine the imaging protocol in further consideration of the second information.

The second information may include identification (ID) information of the object, the first information may include X-ray accumulation amounts for respective portions of the object, and the imaging protocol determiner may determine an imaging portion for the object based on the ID information, and may determine the imaging protocol based on the determined imaging portion, the X-ray accumulation amount included into the first information and corresponding to the determined imaging portion, and an X-ray tolerance for the determined imaging portion.

The first information may include X-ray accumulation amounts for respective portions of the object.

The X-ray apparatus may further include an X-ray radiation amount transmitter for transmitting, to the device of the object, X-ray imaging information including an overall amount of an X-ray radiation irradiated to the object according to the determined imaging protocol via the short range wireless communication.

The X-ray imaging information may further include information of at least one of imaged portions of the object and amounts of the X-ray radiation irradiated to respective imaged portions of the object.

The X-ray imaging information may include information of at least one of a technologist who performed the imaging, a doctor who ordered the imaging, an imaging date, an imaging time, an X-ray image obtained via the determined imaging protocol, and a result of diagnosis based on the X-ray image.

The accumulation information obtainer may receive the X-ray accumulation amount of the object from the device of the object via a near field communication (NFC) as the device of the object is tagged to the X-ray apparatus.

The short range wireless communication may include at least one of a near field communication (NFC), Bluetooth, and Wi-Fi.

According to another exemplary embodiment, there is provided a method of managing X-ray accumulation amount of an object, the method including transmitting information of X-ray accumulation amount of the object to an X-ray apparatus for imaging the object via a designated short range wireless communication method; receiving X-ray imaging information including an amount of X-ray irradiated to the object as the object is imaged by the X-ray apparatus from the X-ray apparatus; and updating information of X-ray accumulation amount of the object by using the X-ray imaging information.

The transmitting the X-ray accumulation amount may include transmitting the X-ray accumulation amount of the object to a device of the object via a near field communication (NFC) as the device of the object is tagged to the X-ray apparatus; and receiving the X-ray imaging information includes receiving the amount of the X-ray radiation of the object from the X-ray apparatus via the NFC as the device of the object is tagged to the X-ray apparatus.

The X-ray accumulation amount may include X-ray accumulation amounts for respective portions of the object.

The method of managing X-ray accumulation amount of an object may further include displaying at least one of the updated X-ray accumulation amount and the X-ray imaging information.

The method of managing X-ray accumulation amount of an object may further include displaying at least one of information of X-ray accumulation amounts regarding respective portions of the object, a number of times that the respective portions of the object have been imaged, and dates at which the respective portions of the object have been imaged.

The method of managing X-ray accumulation amount of an object may further include storing at least one of the updated X-ray accumulation amount and the X-ray imaging information in an external database accessible with authentication of the object.

According to another exemplary embodiment, there is provided a device including an accumulation information transmitter for transmitting information of X-ray accumulation amount of an object to an X-ray apparatus for imaging the object via a designated short range wireless communication method; an X-ray radiation amount receiver for receiving X-ray imaging information including an amount of X-ray irradiated to the object as the object is imaged by the X-ray apparatus via a designated short range wireless communicator; and an accumulation amount updater for updating information of X-ray accumulation amount of the object by using the received accumulation amount.

The accumulation information transmitter may transmit the X-ray accumulation amount of the object to the X-ray apparatus via a near field communication (NFC), when the device of the object is tagged to the X-ray apparatus, and the X-ray radiation amount receiver may receive the X-ray imaging information from the X-ray apparatus via the NFC, when the device of the object is tagged to the X-ray apparatus.

The X-ray accumulation amount may include X-ray accumulation amounts for respective portions of the object.

The device may further include a display for displaying the X-ray imaging information.

The display may display at least one of information of X-ray accumulation amounts for respective portions of the object, a number of times that the respective portions of the object have been imaged, and dates at which the respective portions of the object have been imaged.

The device may store at least one of the updated X-ray accumulation amount and the X-ray imaging information in an external database accessible with authentication of the object.

According to another aspect of the present invention, there is provided a non-transitory computer-readable recording medium having recorded thereon a computer program which, when executed by a computer system, causes the computer system to execute the method of managing X-ray accumulation amount of an object.

According to another aspect of the present invention, there is provided a non-transitory computer-readable recording medium having recorded thereon a computer program which, when executed by a computer system, causes the computer system to execute the X-ray imaging method.

According to another exemplary embodiment, there is provided a tomographic medical apparatus including a storage unit of a portable device for collecting and storing X-ray accumulation amount of an object, a first communicator of the portable device for transmitting, via a short range wireless communication, the X-ray accumulation amount of the object to an imaging apparatus prior to current imaging of the object, a second communicator of the imaging apparatus for transmitting, via the short range wireless communication, an amount of X-ray radiation irradiated to the object during the current imaging of the object, and an accumulation amount updater for updating the X-ray accumulation amount of the object stored in the storage unit based on the amount of X-ray radiation irradiated to the object during the current imaging of the object.

The portable device may further include a display for displaying the X-ray accumulation amount of the object.

The imaging apparatus may include an imaging protocol determiner for designing an imaging protocol for the current imaging of the object based on the transmitted X-ray accumulation amount of the object, to avoid exceeding an allowable radiation dose determined for the object.

BRIEF DESCRIPTION OF THE DRAWINGS

The above and/or other aspects will become more apparent by describing certain exemplary embodiments, with reference to the accompanying drawings, in which:

FIG. 2 is a flowchart showing a method of obtaining an X-ray image according to an exemplary embodiment;

FIG. 3 is a diagram showing an example of an X-ray accumulation amount the X-ray apparatus receives from the device, according to an exemplary embodiment;

FIG. 4 is a diagram showing operations performed between the X-ray apparatus and the device, according to an exemplary embodiment;

FIG. 5 is a diagram showing operations performed between the X-ray apparatus and the external database, according to an exemplary embodiment;

FIG. 6 is a diagram showing an example X-ray imaging information transmitted from the X-ray apparatus to the device, according to an exemplary embodiment;

FIG. 7 is a flowchart showing a method of managing X-ray accumulation amount according to an exemplary embodiment;

DETAILED DESCRIPTION

Figure 1:
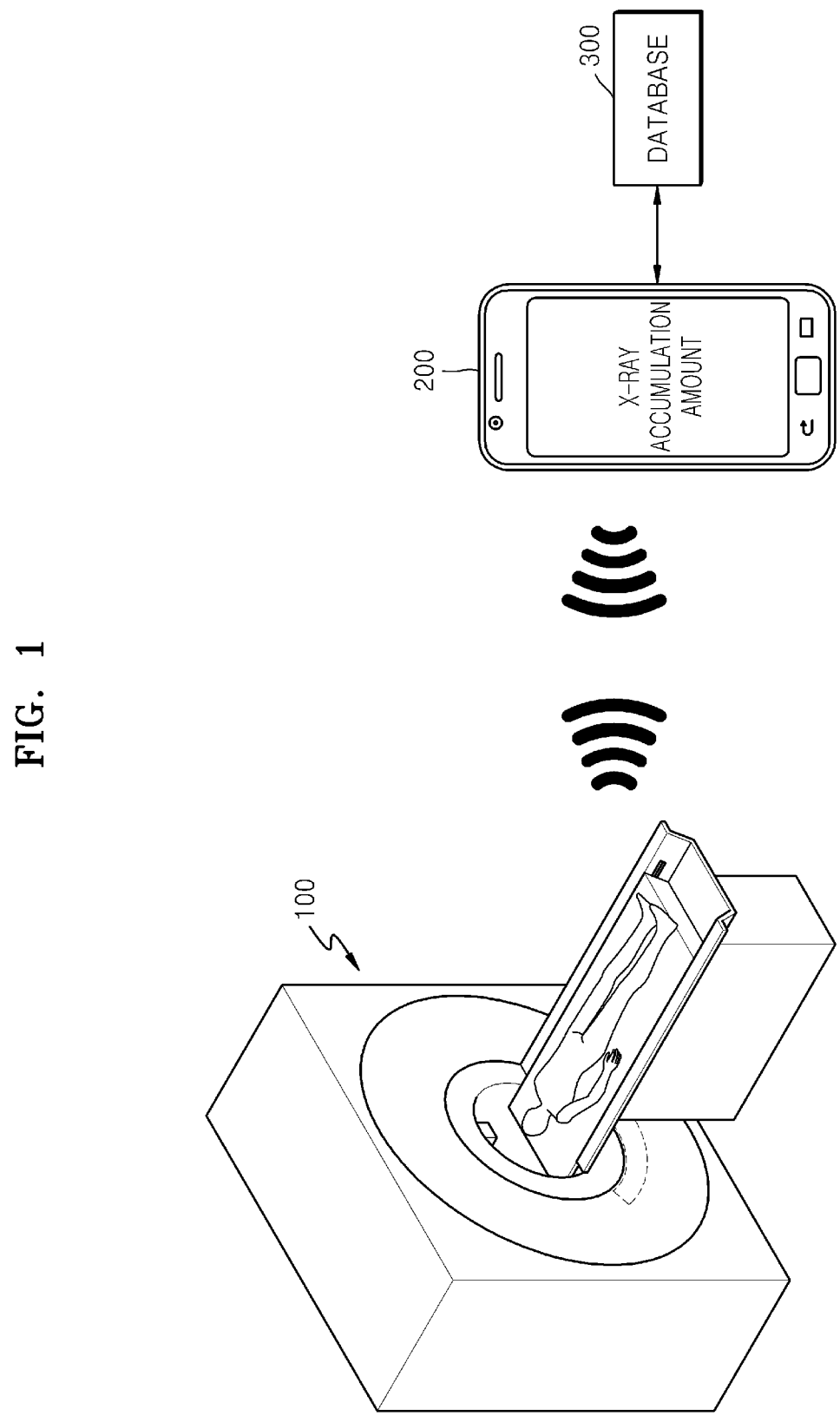
FIG. 1 is a diagram showing an X-ray apparatus and a device according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Unless explicitly described to the contrary, "comprise" and variations such as "comprises" or "comprising" is understood to imply the inclusion of stated elements but not the exclusion of any other elements. In addition, the elements and components described in the specification mean units for processing at least one function and operation and can be implemented by hardware components or software components and combinations thereof.

An image may refer to multi-dimensional data consisting of discrete image elements (e.g., pixels in a two-dimensional (2D) image and voxels in a three-dimensional (3D) image). For example, images may include a medical image of an object obtained via an X-ray apparatus or a CT apparatus.

An object may refer to a human, an animal, or a portion of a human or an animal. A user may refer to a medical expert, which may be a doctor, a nurse, a medical technologist, a medical imaging expert, a radiological technologist, or a medical device repairman, but is not limited thereto.

Referring to FIG. 1, the X-ray apparatus 100 according to an exemplary embodiment may receive information of X-ray accumulation amount of an object from the device 200 via a short range wireless communication. The X-ray apparatus 100 may obtain an X-ray image of the object based on the information of X-ray accumulation amount.

After an X-ray image of the object is obtained, the X-ray apparatus 100 may transmit X-ray imaging information including amount of X-ray irradiated to the object to the device 200 via the short range wireless communication.

The device 200 may update information of X-ray accumulation amount by adding the amount of X-ray radiation received from the X-ray apparatus 100 to existing X-ray accumulation amount.

The X-ray apparatus 100 may receive information of X-ray accumulation amount of the object from the device 200 by reading Barcode or Quick Response (QR) Code, for example, a matrix barcode or a 2D barcode, stored in the device 200.

After an X-ray image of the object is obtained, the X-ray apparatus 100 may write X-ray imaging information including amount of X-ray irradiated to the object in Barcode or QR Code.

The X-ray apparatus 100 may update information of X-ray accumulation amount of the object by adding the amount of X-ray irradiated to the object to the X-ray accumulation amount of the object received from the device 200. The X-ray apparatus 100 may write the updated information of X-ray accumulation amount of the object in Barcode or QR Code.

The X-ray apparatus 100 may transmit the amount of X-ray irradiated to the object and the updated information of X-ray accumulation amount of the object written in Barcode or QR Code to the X-ray apparatus 100.

The X-ray apparatus 100 may be a device for obtaining an X-ray image of an object by irradiating an X-ray to the object. The X-ray apparatus 100 may include an X-ray imaging device, a CT imaging device, a position emission tomography (PET) imaging device, etc. However, an exemplary embodiment is not limited thereto.

The device 200 may be a portable device for managing X-ray management information including information of X-ray accumulation amount. The device 200 may be a mobile phone, a smart phone, a laptop computer, a tablet PC, an e-book terminal, a digital broadcasting terminal, a personal digital assistant (PDA), a portable multimedia player (PMP), a digital camera, etc. However, an exemplary embodiment is not limited thereto.

The X-ray device 100 and the device 200 may include a short range wireless communication apparatus, i.e., a short range wireless communicator or a short range wireless communication interface. The short range wireless communication apparatus may include a Wi-Fi device, a Bluetooth device, a Bluetooth low energy (BLE) device, a ultra wideband (UWB) device, a Zigbee device, a near field communication (NFC) device, a Wi-Fi Direct (WFD) device, an infrared data association (IrDA) device, etc.

FIG. 2 is a flowchart of a method of obtaining an X-ray image according to an exemplary embodiment.

In operation S210, the X-ray apparatus 100 obtains information of X-ray accumulation amount of an object.

The X-ray accumulation amount may include the sum of X-ray amounts irradiated to the object for a particular period of time. The X-ray accumulation amount may include the sum of X-ray accumulations at respective portions of the object.

The X-ray apparatus 100 according to an exemplary embodiment may obtain information of X-ray accumulation amount of an object from the device 200 via a short range wireless communication.

For example, if the X-ray apparatus 100 and the device 200 include NFC modules, a NFC module of the X-ray apparatus 100 and a NFC module of the device 200 may operate in P2P mode. Here, as the NFC module (client) of the device 200 approaches to the NFC module (host) of the X-ray apparatus 100, the device 200 may be tagged by the NFC module of the X-ray apparatus 100 and may transmit information of X-ray accumulation amount of an object to the X-ray apparatus 100.

The X-ray apparatus 100 may receive information other than the X-ray accumulation amount, from the device 200. The information may include identification (ID) of the object, name of the object, medical history of the object, etc.

Since a short range wireless communication is used, the device 200 belonging to an object needs to approach the X-ray apparatus 100, in order to transmit information of X-ray accumulation amount to the X-ray apparatus 100 and the object may personally manage information of X-ray accumulation amount. Therefore, security of medical information may be improved. The object may transmit information of X-ray accumulation amount to the X-ray apparatus 100 without inputting any information.

For example, information regarding X-ray accumulation amount of an object according to an exemplary embodiment may be stored in the external database 300. The external database 300 may receive information of X-ray accumulation amount of the object stored in the device 200 from the device 200 periodically or based on an input of the object.

The X-ray apparatus 100 may obtain X-ray accumulation amount from an external database 300, which shares information with the device 200 of an object, based on authentication information input by the object.

For example, the external database 300 may demand authentication information to authenticate that a device which attempts to access the information regarding X-ray accumulation amount of an object stored in the external database 300 is the device authorized by the object. The authentication information may include at least one of ID of the object, a password, and a URL of the external database 300.

The X-ray apparatus 100 may receive authentication information via an input device, such as a keyboard, a mouse, and/or a touchscreen, or may receive authentication information from the device 200 of an object via a short range wireless communication.

The X-ray apparatus 100 may receive authentication information from an object and may receive information of X-ray accumulation amount of the object from the external database 300 by using the received authentication information.

Because the information of X-ray accumulation amount of the object is stored in the external database 300, the object may transmit the object's X-ray accumulation amount to an X-ray imaging device without the device 200. Furthermore, since information of X-ray accumulation amount of an object may be accessed only based on authentication information of the object, security regarding medical information of the object including information of X-ray accumulation amount may be improved.

In operation S220, the X-ray apparatus 100 may determine an imaging protocol for imaging the object based on the information of X-ray accumulation amount of the object.

The X-ray apparatus 100 may determine a portion of the object to be imaged based on identification information of the object. For example, a portion of the object to be imaged may be determined based on a disease of the object, previous imaging history of the object, or an imaging instruction of a doctor who examined the object.

The X-ray apparatus 100 may adjust an X-ray amount by adjusting the imaging protocol, such that an X-ray accumulation including the amount of an X-ray to be irradiated does not exceed a preset X-ray amount.

In operation S230, the X-ray apparatus 100 may obtain an X-ray image of the object based on the determined imaging protocol.

The X-ray apparatus 100 may measure the amount of an X-ray irradiated to the object during an imaging operation.

FIG. 3 is a diagram showing an example of information of the X-ray accumulation amount the X-ray apparatus 100 receives from the device 200, according to an exemplary embodiment.

Referring to FIG. 3, information regarding X-ray accumulation amount may include information regarding an object, such as an object ID 310, age 314, gender 316, and body weight 318, but this is not limiting. The information regarding X-ray accumulation amount may include an overall accumulated X-ray dose 320, a head accumulated X-ray dose 322, a chest accumulated X-ray dose 324, an abdomen accumulated X-ray dose 326, and a date of the most recent X-ray imaging 328, but this is not limiting.

The object ID 310 is a common object identification information for X-ray accumulation amount management in the X-ray apparatus 100, the device 200, and the external database 300 and each object may be allocated a unique value.

Each of the overall accumulated X-ray dose 320, head accumulated X-ray dose 322, chest accumulated X-ray dose 324, and abdomen accumulated X-ray dose 326 may include a sum of accumulated X-ray radiation to the object for a predetermined period of time (e.g., one year).

Based on identification information of the object, for example, the object ID 310 and/or the object name 312, the X-ray apparatus 100 may determine whether the object corresponding to information regarding X-ray accumulation amount transmitted to the X-ray apparatus 100 is identical to the object to be X-rayed.

As described above, the X-ray apparatus 100 may determine an imaging protocol based on at least one of the overall accumulated X-ray dose 320, head accumulated X-ray dose 322, chest accumulated X-ray dose 324, and abdomen accumulated X-ray dose 326.

The X-ray apparatus 100 may determine an imaging protocol by further considering information including age, gender, and body weight of an object. For example, if an adult and a child have a same X-ray accumulation, the X-ray apparatus 100 may select an imaging protocol with less X-ray exposure for the child as compared to the adult.

The X-ray apparatus 100 may determine an imaging protocol based on the most recent X-ray imaging date 328. For example, an imaging protocol with less X-ray exposure may be selected for an imaging date that is more recent.

The information regarding X-ray accumulation may further include information regarding medical problems of the object, and a history of X-ray imaging of the object.

The information shown in FIG. 3 may be converted into an appropriate form according to devices for transmitting and receiving the information. For example, if the information shown in FIG. 3 is transmitted from the device 200 to the X-ray apparatus 100 via NFC communication, the device

200 may convert the information into NFC data exchange format (NDEF) and transmit the converted information. Furthermore, if the information shown in FIG. 3 is transmitted from the external database 300 to the X-ray apparatus 100, the external database 300 may convert information into a markup language, such as XML, and transmit the converted information.

FIG. 4 is a diagram showing operations performed between the X-ray apparatus 100 and the device 200, according to an exemplary embodiment.

In operation S410, the X-ray apparatus 100 and the device 200 establish a short range wireless communication channel. In operation S420, the X-ray apparatus 100 receives information regarding X-ray accumulation amount of an object from the device 200. In operation S430, the X-ray apparatus 100 determines an imaging protocol for the object based on the received information. In operation S440, the X-ray apparatus 100 obtains an X-ray image of the object according to the determined imaging protocol. Since the operations S410 through S440 are identical to the description given above with reference to FIG. 2, detailed descriptions thereof will be omitted.

After the imaging operation, in operation S450, the X-ray apparatus 100 may establish a short range wireless communication channel to the device 200 based on an access of the device 200 or a request from the device 200.

In operation S460, the X-ray apparatus 100 may transmit X-ray imaging information including an amount of X-ray irradiated to the object in the X-ray imaging operation to the device 200.

The amount of X-ray irradiated to the object may include an amount of X-ray irradiated to the object when the object is imaged according to the imaging protocol determined in the operation S430.

The X-ray imaging information transmitted to the device 200 may further include information of at least one of imaged body portions of the object and amounts of X-rays irradiated to the respective body portions.

The X-ray imaging information transmitted to the device 200 may further include information of at least one of a technologist who performed the imaging operation, a doctor who ordered the imaging operation, current imaging date, current imaging time, X-ray imaging dates on which the object has been imaged, an X-ray image obtained via the determined imaging protocol, and a result of diagnosis using the X-ray image.

In operation S470, the device 200 may update an X-ray accumulation amount of the object by adding the amount of X-ray irradiated to the object to the previously stored X-ray accumulation amount.

According to the exemplary embodiment of FIG. 4, X-ray accumulation amount of an object is managed by the device 200 of the object, and thus the object may calculate the accurate X-ray accumulation amount. Furthermore, since an access to the X-ray accumulation amount of the object may be restricted by the object, possibility of unauthorized disclosure of X-ray accumulation amount may be prevented.

FIG. 5 is a diagram showing operations performed between the X-ray apparatus 100 and the external database 300, according to an exemplary embodiment. The above-described operations and functions are applicable here and will be not repeated.

In operation S510, the X-ray apparatus 100 may receive authentication information from an object for authenticating the object. The authentication information may be received as an object input from the device 200 via a short range wireless communication.

In operation S520, the X-ray apparatus 100 may transmit received authentication information of the object to the external database 300. In operation S530, the X-ray apparatus 100 may receive an authorization for accessing data of the object.

In operation S540, the X-ray apparatus 100 may receive information regarding X-ray accumulation amount of the object from the external database 300 based on the received access authorization. In operation S550, the X-ray apparatus 100 may determine an imaging protocol based on the received information of X-ray accumulation amount of the object. In operation S560, the X-ray apparatus 100 may perform an X-ray imaging of the object according to the determined imaging protocol. Since the operations S540 through S560 are identical to those described above with reference to FIGS. 2 and 4, detailed descriptions thereof will be omitted.

In operation S570, the device 200 may update an X-ray accumulation amount of the object by adding the amount of X-ray irradiated to the object to the previous X-ray accumulation amount stored in the external database 300.

FIG. 6 is a diagram showing an example of the X-ray imaging information transmitted from the X-ray apparatus 100 to the device 200, according to an exemplary embodiment.

As described above, the X-ray apparatus 100 may transmit X-ray imaging information including an amount of X-ray irradiated to an object to the device 200 or the external database 300.

The X-ray imaging information may include the object ID 310, the object name 312, an amount of X-ray radiation dose 614, a region of the object to which X-rays are irradiated 616, and an imaging date 618.

The device 200 may update information of X-ray accumulation amount of an object based on the amount of the X-ray radiation dose 614 and may store X-ray imaging information including the amount of the X-ray radiation dose 614. The device 200 may provide X-ray the amount of X-ray radiation dose 614 to the object.

FIG. 7 is a flowchart of a method of managing X-ray accumulation amount according to an exemplary embodiment. The above-described operations and functions are applicable here and will be not repeated.

In operation S710, the device 200 transmits information of X-ray accumulation amount of an object stored in the device 200 to the X-ray apparatus 100 via a short range wireless communication method.

For example, both the X-ray apparatus 100 and the device 200 may include NFC modules, and the two NFC modules may operate in P2P mode. Therefore, as the NF module (client) of the device 200 approaches to the NFC module (host) included in the X-ray apparatus 100, the device 200 may be tagged by the NFC module included in the X-ray apparatus 100 and may transmit information of X-ray accumulation amount of an object to the X-ray apparatus 100.

The device 200 may transmit information of the object to the X-ray apparatus 100.

The information regarding X-ray accumulation amount of the object stored in the device 200 may include X-ray accumulation amounts regarding respective body portions of the object.

In operation S720, the device 200 may receive X-ray imaging information including an amount of X-ray irradiated to the object from the X-ray apparatus 100 via a short range wireless communication method.

In operation S730, the device 200 may update an X-ray accumulation amount of the object by using the received amount of X-ray irradiated to the object.

The device 200 may update an X-ray accumulation amount of the object by adding the amount of X-ray irradiated to the object received from the X-ray apparatus 100 to the previously stored X-ray accumulation amount.

The device 200 may update X-ray accumulation amounts regarding the respective imaged portions of the object by respectively adding the amounts of X-rays irradiated to the respective imaged portions of the object to the previously stored X-ray accumulation amounts regarding the respective imaged portions of the object.

The device 200 may store X-ray imaging information received from the X-ray apparatus 100 in correspondence to imaging dates, technologists in charge, doctors who ordered the X-ray imaging operations, or hospitals at which imaging operations took place.

Figure 8:
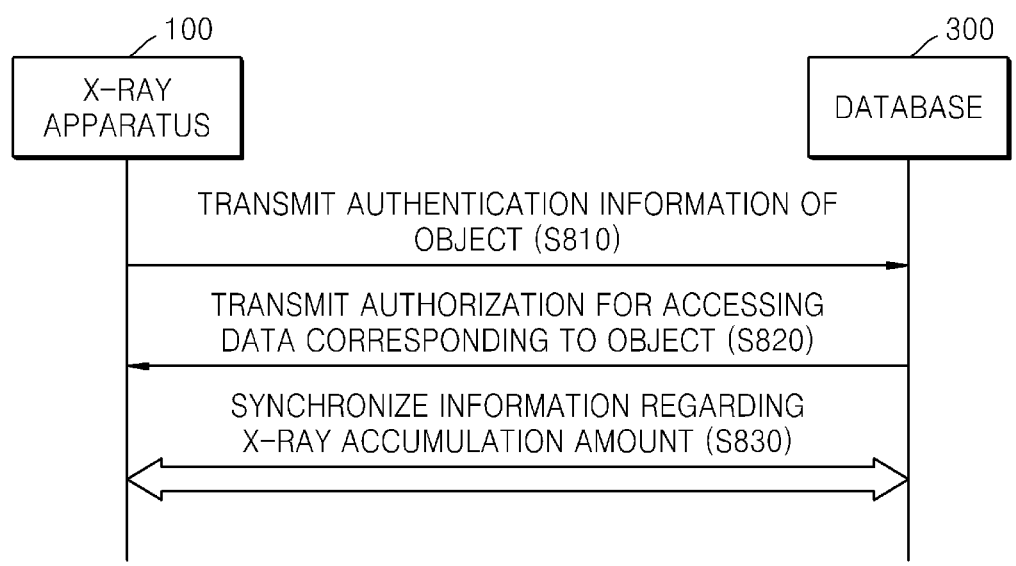
FIG. 8 is a diagram showing operations performed between the device and the external database, according to an exemplary embodiment.

FIG. 8 is a diagram showing operations performed between the device 200 and the external database 300, according to an exemplary embodiment.

The device 200 may perform data synchronization regarding information of X-ray accumulation amount of an object with the external database 300 that may be accessed based on authentication of the object.

In operation S810, the device 200 may transmit authentication information for authenticating an object to the external database 300.

In operation S820, the device 200 may receive an authorization for accessing data of the object from the external database 300.

In operation S830, the device 200 performs data synchronization of X-ray accumulation amounts of an object with the external database 300 based on the access authorization received from the external database 300.

For example, if it is determined that the X-ray accumulation amounts stored in the device 200 are more recent than the X-ray accumulation amounts stored in the external database 300, the device 200 may update the information regarding X-ray accumulation amounts of the object stored in the external database 300 to correspond to the information of X-ray accumulation amounts stored in the device 200.

If it is determined that the X-ray accumulation amounts of the object stored in the external database 300 is more recent than the X-ray accumulation amounts stored in the device 200, the device 200 may update the information regarding X-ray accumulation amounts of the object stored in the device 200 to correspond to the information regarding X-ray accumulation amounts stored in the external database 300.

The device 200 may synchronize information regarding X-ray accumulation amount of an object with the external database 300 based on an user input or may periodically synchronize information regarding X-ray accumulation amount of an object with the external database 300 without a user input.

Therefore, the device 200 may perform data synchronization regarding information of X-ray accumulation amount of an object by periodically comparing information of X-ray accumulation amount stored in the device 200 with the information of X-ray accumulation amount stored in the external database 300 and update with more recently stored information regarding X-ray accumulation amount of the object.

The device 200 may store X-ray accumulation amount, and also X-ray imaging information received from the X-ray apparatus 100 in the external database 300. For example, the device 200 may store information regarding a technologist who performed the imaging operation, a doctor who ordered the imaging operation, imaging dates, imaging times, etc., in the external database 300.

Since information of X-ray accumulation amount of the object stored in the external database 300 may only be accessed via authentication of the object, the information of X-ray accumulation amount of the object may be managed by the object only. Therefore, security of medical information including X-ray accumulation amount may be improved.

Because the information of X-ray accumulation amount is synchronized between the device 200 and the external database 300, the object may obtain information of X-ray accumulation amount from the external database 300 even without the device 200. Furthermore, because the object backs up information of X-ray accumulation amount collected via the device 200 to the external database 300, more precise information of X-ray accumulation amount may be obtained. Furthermore, even if the X-ray apparatus 100 directly stores information of X-ray accumulation amount of the object in the external database 300, the device 200 may update information of X-ray accumulation amount of the object by synchronizing the information of X-ray accumulation amount.

FIGS. 9 to 12 are diagrams showing X-ray management information displayed by the device 200.

Figure 9:
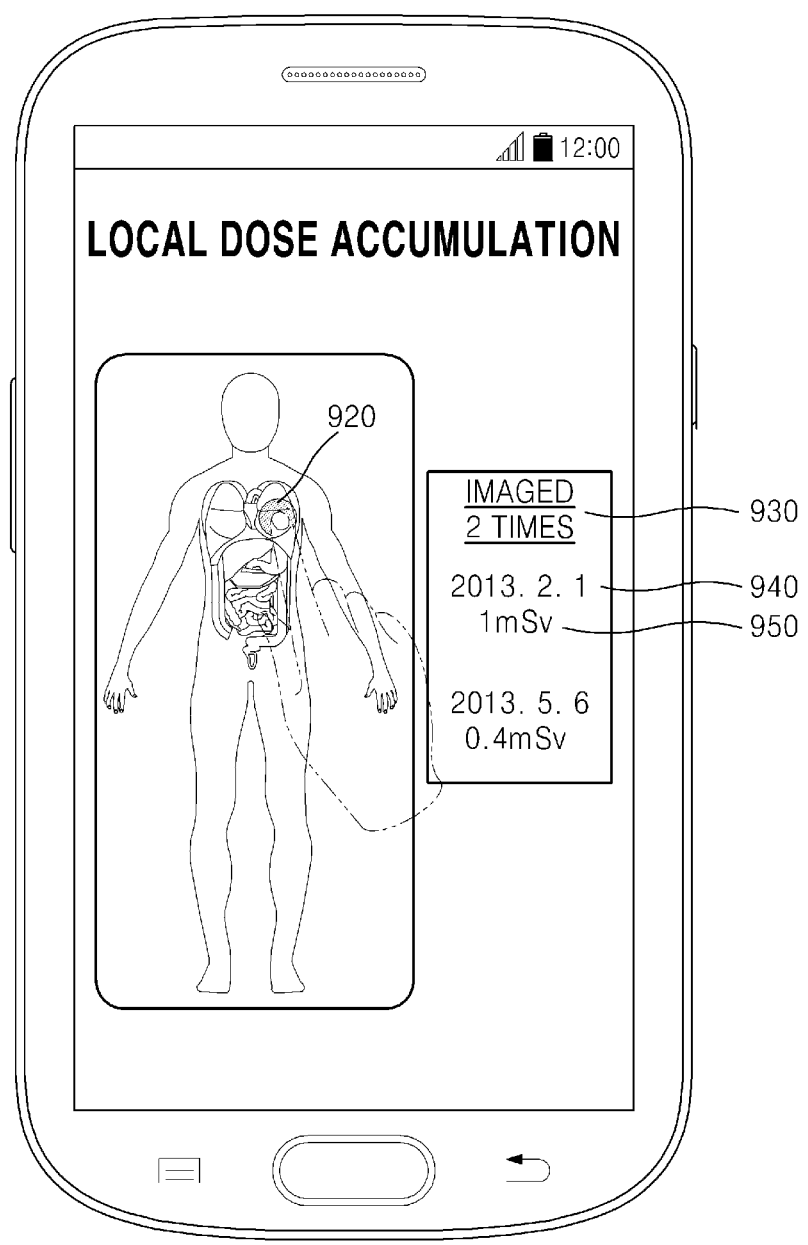
FIGS. 9, 10, 11, and 12 are diagrams showing X-ray management information displayed by the device.

As shown in FIG. 9, the device 200 may provide information regarding X-ray accumulation amounts regarding respective portions of an object. For example, the device 200 may display information regarding X-ray accumulation amounts regarding respective body portions of an object to the object via texts, numbers, graphs, and/or graphic user interfaces (GUIs).

An X-ray accumulation amount regarding a portion of an object may be amount of X-ray accumulated at the corresponding portion for a preset period of time (e.g., 1 year.) The device 200 may change the preset period of time based on an input from an object.

If a user input (i.e., a touchscreen input) selects the breast 920 of a human figure image displayed at the device 200, the device 200 may provide the number of times 930 that X-rays are irradiated to the breast of the object, the dates 940 at which the X-rays are irradiated to the breast, and an amount of X-ray 950 irradiated to the breast during a preset period of time.

Figure 10:
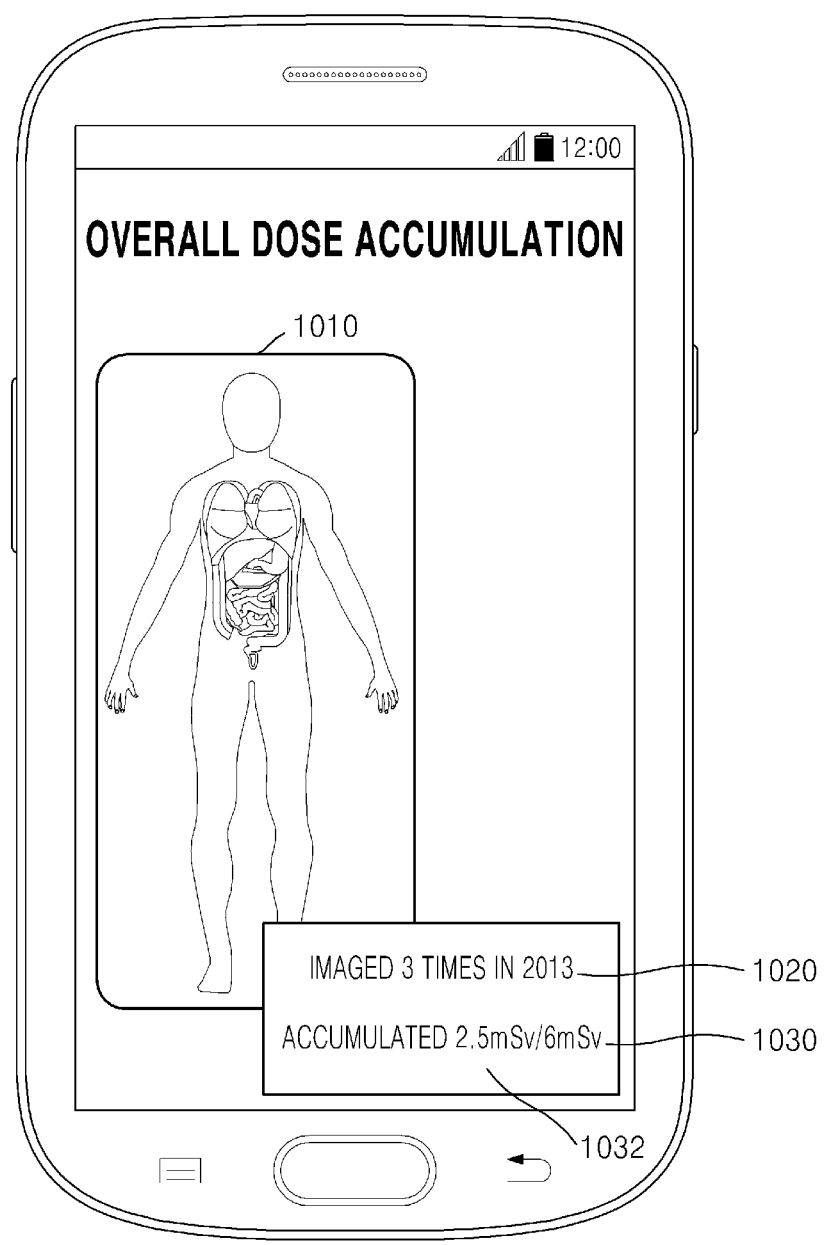

As shown in FIG. 10, the device 200 may provide information regarding the overall X-ray accumulation amount of an object. The device 200 may display information regarding X-ray accumulation on a human figure image 1010.

The device 200 may provide the number 1020 of times the X-rays have been irradiated to the object, an X-ray radiation tolerance 1030 to a human body for the preset period of time, and an amount 1032 of X-ray accumulated by the object for a preset period of time. For example, an X-ray tolerance may be an allowable safe amount of X-ray radiation allowed for a particular object, or a portion of an object, depending on gender, weight, age, environmental factors, etc.

Figure 11:
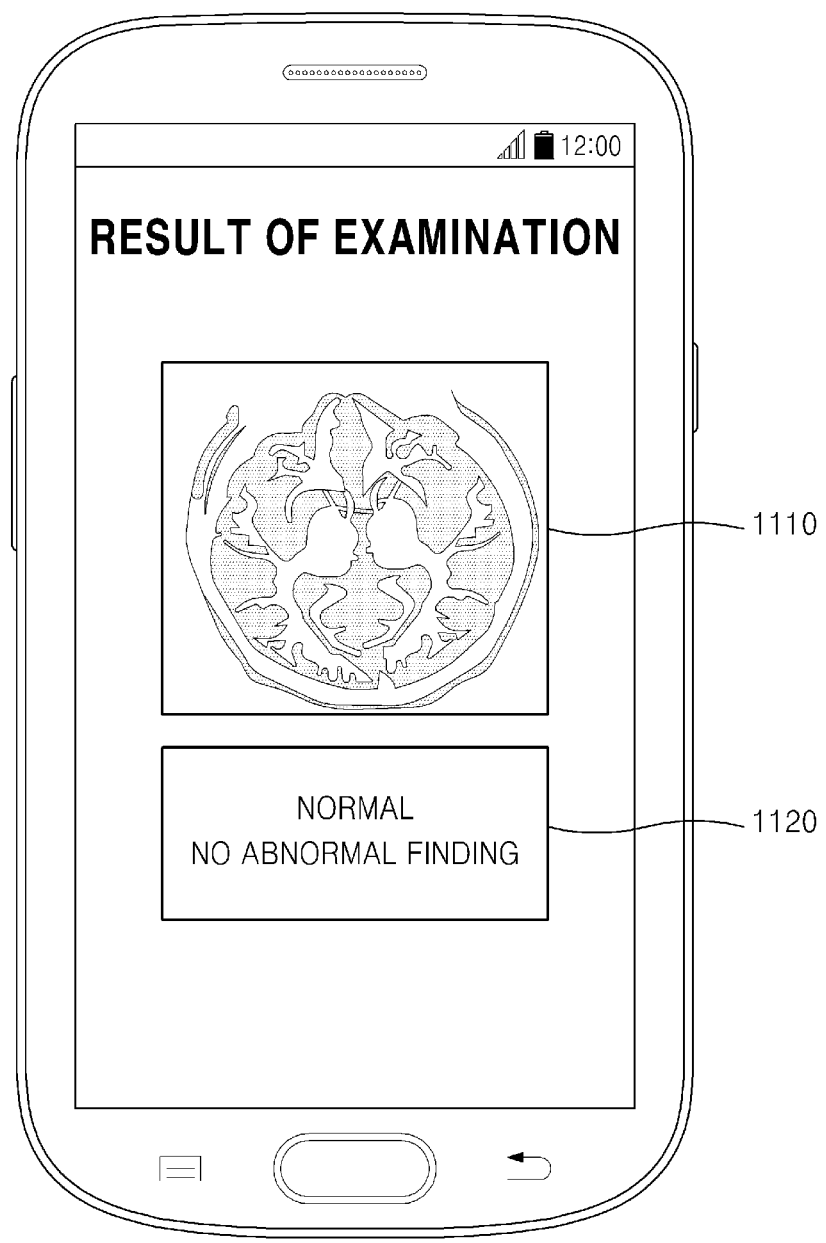

As shown in FIG. 11, the device 200 may provide a result of examination related to an X-ray imaging. The device 200 may provide an X-ray image 1110 of an object obtained via an X-ray imaging. The device 200 may provide a result 1020 of an examination based on the X-ray image 1110.

Figure 12:
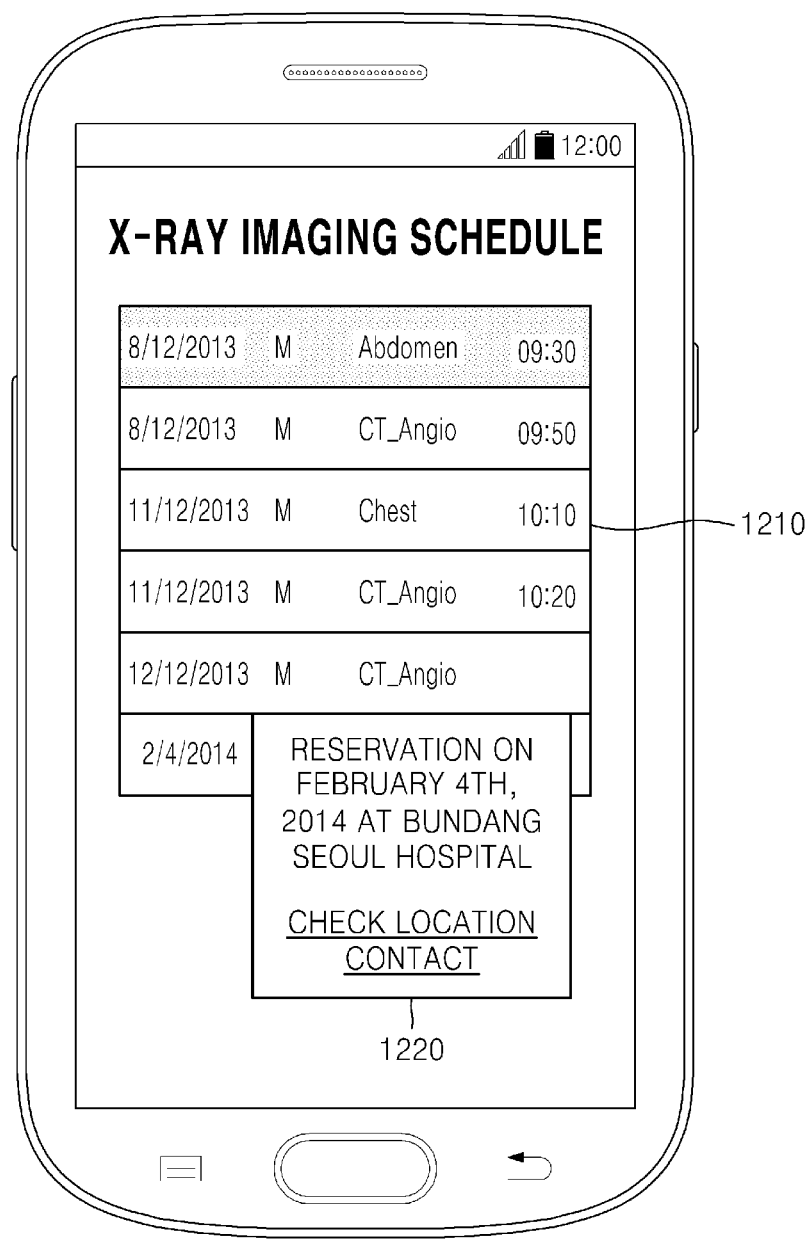

As shown in FIG. 12, the device 200 may provide a list 1210 showing dates of the X-ray imaging of the object. When an object selects one of the X-ray imaging dates, the device 200 may provide schedule information 1220 including a corresponding hospital and a reservation date.

Figure 13A:
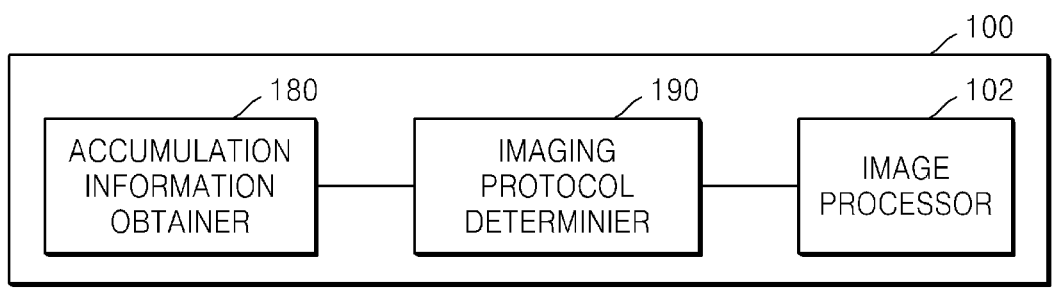
FIG. 13A is a diagram showing the configuration of the X-ray apparatus according to an exemplary embodiment.

FIG. 13A is a diagram showing a detail of the X-ray apparatus 100 according to an exemplary embodiment.

Referring to FIG. 13A, the X-ray apparatus 100 may include an accumulation information obtainer 180, an imaging protocol determiner 190, and a scanner 102. The components and functions of the X-ray apparatus 100 which are described in detail above will not be repeated.

The accumulation information obtainer 180 may obtain information regarding X-ray accumulation amount of an object from the device 200 via a short range wireless communication method. As another example, the accumulation information obtainer 180 may obtain information of X-ray accumulation amount of an object from the external database 300 based on authentication information obtained from the object.

The imaging protocol determiner 190 may determine an imaging protocol for imaging the object based on the information of X-ray accumulation amount of the object obtained by the accumulation information obtainer 180. The imaging protocol determiner 190 may determine an imaging protocol by further including information of the object. The imaging protocol determiner 190 may determine imaging protocols regarding respective portions of the object based on preset X-ray radiation tolerances for the respective portions of the object.

The scanner 102 may obtain a medical image of the object based on the imaging protocol determined by the imaging protocol determiner 190.

Figure 13B:
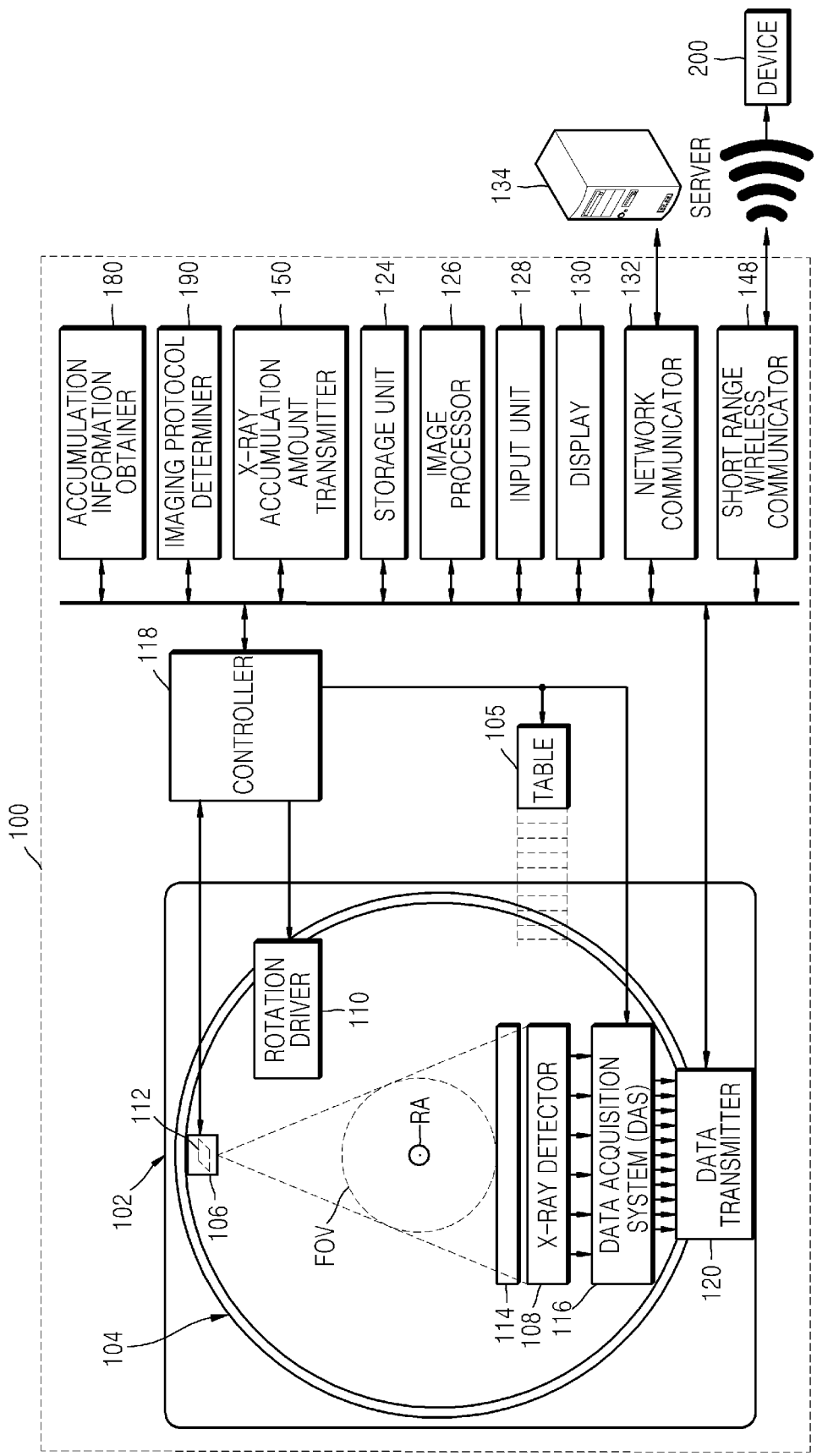
FIG. 13B is a diagram showing the configuration of the X-ray apparatus according to an exemplary embodiment.

FIG. 13B is a diagram showing the configuration of the X-ray apparatus 100 according to an exemplary embodiment.

Referring to FIG. 13B, the X-ray apparatus 100 may include a network communicator 132, a short range wireless communicator 148, an X-ray accumulation amount transmitter 150, a table 105, a controller 118, a storage unit 124, an image processor 126, an input unit 128, and a display 130, the accumulation information obtainer 180, the imaging protocol determiner 190, and the scanner 102.

The scanner 102 according to an exemplary embodiment may include a rotating frame 104, an X-ray generator 106, an X-ray detector 108, a rotation driver 110, a data acquisition system 116, and a data transmitter 120.

The scanner 102 may include the ring-type rotating frame 104 that may revolve around a designated rotation axis (RA). The rotating frame 104 may have a disc-like shape.

The rotating frame 104 may include the X-ray generator 106 and the X-ray detector 108 that are arranged to face each other and to have designated fields of view (FOV). The rotating frame 104 may include an anti-scatter grid 114 which may be located between the X-ray generator 106 and the X-ray detector 108.

In the X-ray apparatus 100, X-ray radiation reaching a detector (or a photosensitive film) includes attenuated primary radiation that forms a useful image, and scattered radiation that deteriorates image quality. To transmit most of primary radiation and reduce scattered radiation, an anti-scatter grid 114 may be located between a patient and a detector (or a photosensitive film).

For example, the anti-scatter grid may be formed by alternately stacking interspace materials including strips of lead foil, a solid polymer material, a solid polymer, and a fiber composite material. However, an exemplary embodiment is not limited thereto.

The rotating frame 104 may receive a driving signal from the rotation driver 110 and may rotate the X-ray generator 106 and the X-ray detector 108 at a rotation speed. The rotating frame 104 may contact-receive a driving signal and power from the rotation driver 110 via a slip ring (not shown). As another example, the rotating frame 104 may receive a driving signal or power from the rotation driver 110 via a wireless communication.

The X-ray generator 106 may receive a voltage and a current from a power distribution unit (PDU) via a slip ring (not shown) and a high voltage generator (not shown) and generate and emit an X-ray. When the high voltage generator applies a tube voltage, the X-ray generator 106 may generate X-rays having a plurality of energy spectrums in correspondence to the tube voltage.

An X-ray generated by the X-ray generator 106 may be emitted in a designated form via a collimator 112.

The X-ray detector 108 may include a plurality of X-ray detecting elements. A single X-ray detecting element may form a single channel. However, an exemplary embodiment is not limited thereto.

The X-ray detector 108 detects an X-ray that is generated by the X-ray generator 106 and transmitted via an object and may generate electric signals in correspondence to the intensity of the detected X-ray.

The X-ray detector 108 may include an indirect detector which converts radiation into light and a direct detector which directly converts radiation into electric charges. An indirect X-ray detector may include a scintillator. A direct X-ray detector may include a photon counting detector. A data acquisition system (DAS) 116 may be connected to the X-ray detector 108 to collect electric signals generated by the X-ray detector 108 via a wire or wirelessly. Furthermore, electric signals generated by the X-ray detector 108 may be provided to an analog to digital converter (not shown) via an amplifier (not shown).

Based on slice thickness or the number of slices, only a portion of data collected by the X-ray detecting unit 108 may be provided to the image processing unit 126 or only a portion of data may be selected at the image processing unit 126.

A digital signal may be provided to the image processing unit 126 by the data transmitting unit 120 via a wire or wirelessly.

The controller 118 according to an exemplary embodiment may control operations of elements of the X-ray apparatus 100. For example, the controller 118 may control operations of the table 105, the rotation driver 110, the collimator 112, the data acquisition system 116, the storage unit 124, the image processor 126, the input unit 128, the display 130, and the network communicator 132.

The image processor 126 receives data obtained from the data acquisition system 116 (e.g., unprocessed pure data) via the data transmitter 120 and performs pre-processes.

The pre-processes may include a process for correcting sensitivity inconsistency between channels, a process for correcting signal loss due to rapid decrease of signal intensity or an X-ray absorbing material, such as a metal, etc.

Data output by the image processor 126 may be referred to as raw data or projection data. The projection data may be stored in the storage unit 124 together with imaging conditions at the time of data acquisition (e.g., a tube voltage, an imaging angle, etc.).

The projection data may be a group of data values respectively corresponding to intensities of X-rays transmitted through an object. For convenience of explanation, a group of projection data simultaneously obtained at a same imaging angle with respect to all channels is referred to as a projection data set.

The storage unit 124 may include at least one of storage media, such as a flash memory type, a hard disk type, a multimedia card micro type, a card-type memory (e.g., a SD memory, an XD memory, etc.), a random access memory (RAM), a static RAM (SRAM), a read-only memory (ROM), an electrically erasable and programmable read-only memory (EEPROM), a programmable ROM (PROM), a magnetic memory, a magnetic disk, and an optical disk.

The image processor 126 may reconstruct a cross-section image of an object by using an obtained projection data set. The cross-sectional image may be a 3D image. The image processor 126 may generate a 3D image of an object via cone beam reconstruction based on the obtained projection data set.

External inputs including X-ray tomography imaging conditions and image processing conditions may be received via the input unit 128. For example, the X-ray tomography imaging conditions may include a plurality of tube voltages, energy value settings regarding a plurality of X-rays, imaging protocol selection, image reconstruction method selection, FOV region settings, the number of slices, slice thickness, image post-processing parameter settings, etc. Image processing conditions may include image resolution, attenuation coefficient settings regarding images, image combination ratio settings, etc. External inputs regarding authentication information of an object or identification information of the object may be received via the input unit 128.

The input unit 128 may include a device for receiving an input. For example, the input unit 128 may include a microphone, a keyboard, a mouse, a joystick, a touchpad, a touch pen, a voice or gesture recognition device, etc.

The display 130 may display an X-ray image reconstructed by the image processor 126.

Transmissions and receptions of data and power between the elements described above may be performed by using at least one of a wired communication, a wireless communication, and an optical communication.

The network communicator 132 may perform communications with the device 200 and an external medical device via a server 134.

The network communicator 132 may be connected to a network via a wire or wirelessly and perform communications with the server 134 and/or the device 200. The network communicator 132 may exchange data with a hospital server or another device in a hospital connected via a picture archiving and communication system (PACS).

The network communicator 132 may perform data communication with an external device via the digital imaging and communications in medicine (DICOM) standard.

The network communicator 132 may transmit and receive data related to diagnosis of an object via a network. The network communicator 132 may transmit and receive medical images obtained at other medical devices, such as an MRI or an X-ray.

The network communicator 132 may receive a medical history or a treatment schedule regarding a patient from the server 134 and use the received information for clinical diagnosis of the patient.

The short range wireless communicator 148 may be connected to an external device including a short range wireless communication device and perform a short range communication via various short range wireless communication methods described above with reference to FIG. 2.

The accumulation information obtainer 180 may obtain information of X-ray accumulation amount of an object via the short range wireless communicator 148. The accumulation information obtainer 180 may obtain information of X-ray accumulation amount of an object from the external database 300 via the network communicator 132 based on authentication information obtained from the object.

Figure 14A:
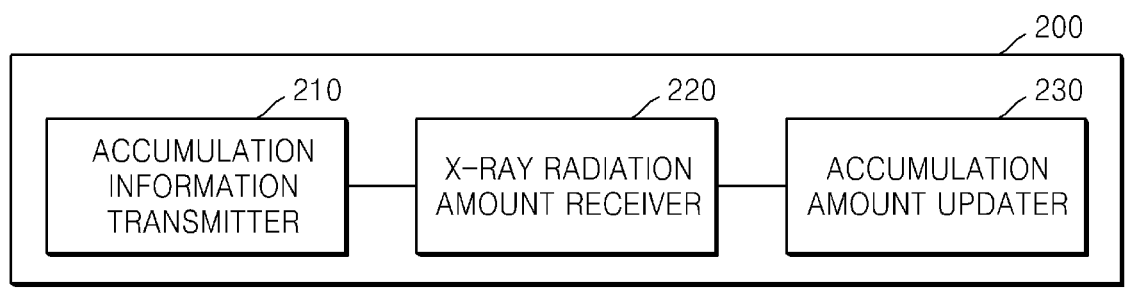
FIG. 14A is a diagram showing the configuration of the device according to an exemplary embodiment.

FIG. 14A is a diagram showing the configuration of the device 200 according to an exemplary embodiment.

As shown in FIG. 14A, the device 200 may include an accumulation information transmitter 210, an X-ray radiation amount receiver 220, and an accumulation amount updater 230. The components and functions of the device 200 which are described in detail above will not be repeated.

The accumulation information transmitter 210 may transmit information of X-ray accumulation amount of an object to the X-ray apparatus 100 by using a short range wireless communication.

The X-ray radiation amount receiver 220 may receive X-ray imaging information including an amount of X-ray irradiated to the object from the X-ray apparatus 100 via a short range wireless communication.

The accumulation amount updater 230 may update an X-ray accumulation amount of the object by using the received amount of the irradiated X-ray.

Figure 14B:
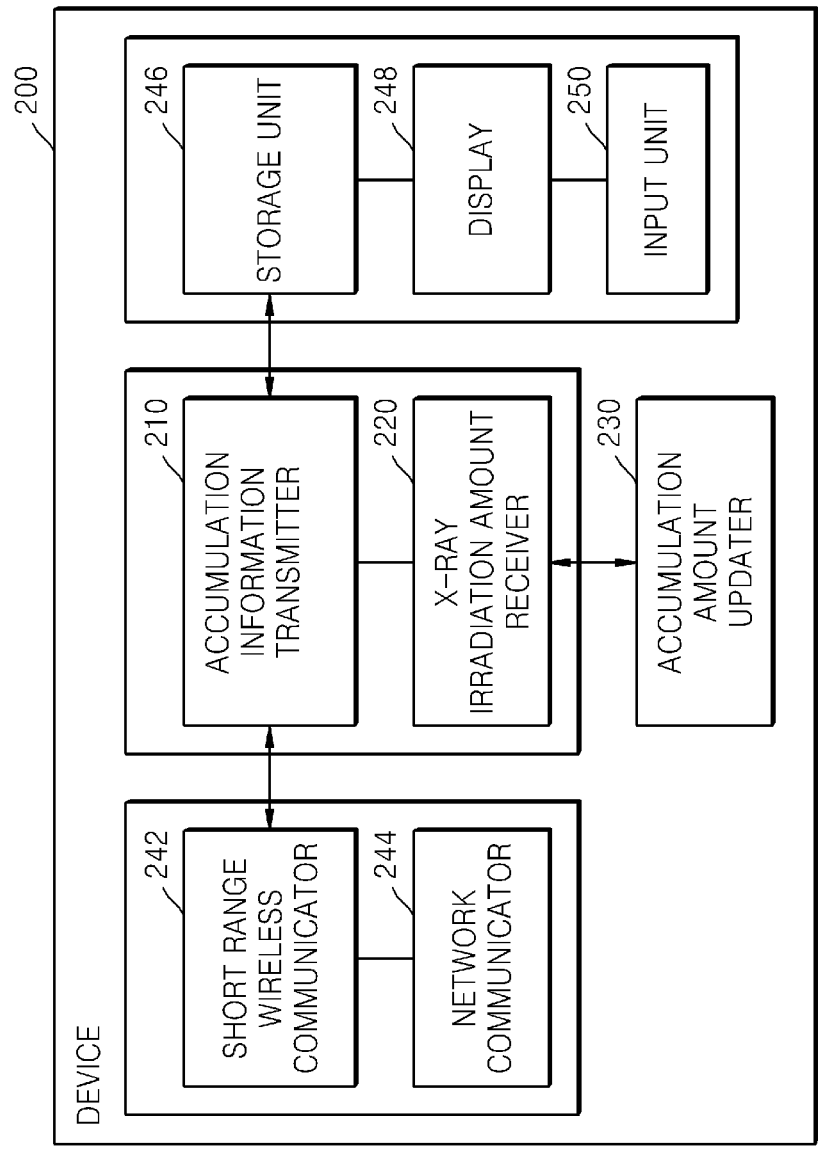
FIG. 14B is a diagram showing the configuration of the device according to an exemplary embodiment.

FIG. 14B is a diagram showing the configuration of the device 200 according to an exemplary embodiment.

As shown in FIG. 14B, the device 200 may include a short range wireless communicator 242, a network communicator 244, a storage unit 246, a display 248, and an input unit 250 other than the accumulation information transmitter 210, the X-ray radiation amount receiver 220, and the accumulation amount updater 230.

The short range wireless communicator 242 may use at least one of various short range wireless communication methods described above with reference to FIG. 2.

The network communicator 244 may be connected to an external network and transmit and receive information of X-ray accumulation amount of an object stored in the external database 300.

The storage unit 246 may store information regarding X-ray accumulation amount and/or medical information of the object. The storage unit 246 may store information received from the external database 300 and/or the X-ray apparatus 100.

The display 248 may display X-ray accumulation amounts and X-ray imaging information of an object. The display 248 may display at least one of information of X-ray accumulation amounts regarding body portions of the object, the numbers of times that the body portions of the object are imaged, and dates at which the respective portions of the object are imaged.

The display 248 may include a cathode ray tube (CRT) display, a liquid-crystal display (LCD), a plasma display panel (PDP), a light emitting diode (LED) display, an organic LED (OLED) display, a field emission display (FED), a vacuum fluorescent display (VFD), a digital light processing (DLP) display, a primary flight display (PFD), a 3D display, a transparent display, or any other appropriate display. The display 248 may be used as an output device, and as an input device, e.g., a touchscreen.

The input unit 250 may receive inputs for managing information of X-ray accumulation amount from an object.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A method of X-ray imaging by controlling an X-ray apparatus comprising:
   obtaining, by the X-ray apparatus, first information comprising an X-ray accumulation amount of an object;
   determining, the X-ray apparatus, an imaging protocol for imaging the object based on the obtained first information; and
   acquiring, the X-ray apparatus, an X-ray image of the object based on the determined imaging protocol,
   wherein the first information including the X-ray accumulation amount of the object is obtained from a device storing information associated with the object via a short range wireless communication.

2. The method of X-ray imaging of claim 1,
   wherein the first information comprises X-ray accumulation amounts for respective portions of the object, and
   the determining the imaging protocol comprises:
   determining an imaging portion of the object; and
   determining the imaging protocol based on the determined imaging portion, the X-ray accumulation amount included in the first information and corresponding to the determined imaging portion, and an X-ray tolerance for the determined imaging portion.

3. The method of X-ray imaging of claim 1, further comprising:
   transmitting, to the device storing information associated with the object, X-ray imaging information including an overall amount of an X-ray radiation irradiated to the object according to the determined imaging protocol, via the short range wireless communication.

4. The method of X-ray imaging of claim 3, wherein the X-ray imaging information further comprises information of at least one of imaged portions of the object and amounts of the X-ray radiation irradiated to respective imaged portions of the object.

5. The method of X-ray imaging of claim 3, wherein the X-ray imaging information further comprises information regarding at least one of a technologist who performed the imaging, a doctor who ordered the imaging, an imaging date, an imaging time, an X-ray image obtained via the determined imaging protocol, and a result of diagnosis based on the X-ray image.

6. The method of X-ray imaging of claim 1, wherein the obtaining the first information comprises:
   receiving the X-ray accumulation amount of the object from the device storing information associated with the object via a near field communication (NFC) as the device storing information associated with the object is tagged to an X-ray apparatus which performs the X-ray imaging.

7. The method of X-ray imaging of claim 1, wherein the short range wireless communication comprises at least one of a near field communication (NFC), Bluetooth, and Wi-Fi.

8. A non-transitory computer-readable recording medium having recorded thereon a computer program which, when executed by a computer system, causes the computer system to execute the method of claim 1.

9. The X-ray imaging method of claim 1,
   wherein the first information further comprises second information regarding the object including at least one of an object ID, a name of the object, an age of the object, a gender of the object, and a body weight of the object, and
   wherein the determining of the imaging protocol comprises:
   identifying whether the object corresponding to information regarding X-ray accumulation amount transmitted to the X-ray apparatus is identical to the object to be X-rayed, based on the second information; and
   determining the imaging protocol based on the second information, according to a result of the identifying.

10. An X-ray apparatus comprising:
    an accumulation information obtainer configured to obtain first information comprising an X-ray accumulation amount of an object;
    an imaging protocol determiner configured to determine an imaging protocol for imaging the object based on the obtained first information;
    a scanner configured to acquire an X-ray image of the object based on the determined imaging protocol; and
    a short-range wireless communicator,
    wherein the first information comprising the X-ray accumulation amount of the object is obtained from a device storing information associated with the object via the short range wireless communicator.

11. The X-ray apparatus of claim 10,
    wherein the first information comprises X-ray accumulation amounts for respective portions of the object, and
    the imaging protocol determiner is configured to determine an imaging portion for the object, and determine the imaging protocol based on the determined imaging portion, the X-ray accumulation amount included in the first information and corresponding to the determined imaging portion, and an X-ray tolerance for the determined imaging portion.

12. The X-ray apparatus of claim 10, further comprising:
    an X-ray radiation amount transmitter configured to transmit, to the device storing information associated with the object, X-ray imaging information including an overall amount of an X-ray radiation irradiated to the object according to the determined imaging protocol via the short range wireless communication.

13. The X-ray apparatus of claim 12, wherein the X-ray imaging information further comprises information of at least one of imaged portions of the object and amounts of the X-ray radiation irradiated to respective imaged portions of the object.

14. The X-ray apparatus of claim 12, wherein the X-ray imaging information comprises information of at least one of a technologist who performed the imaging, a doctor who ordered the imaging, an imaging date, an imaging time, an X-ray image obtained via the determined imaging protocol, and a result of diagnosis based on the X-ray image.

15. The X-ray apparatus of claim 10, wherein the accumulation information obtainer is configured to receive the X-ray accumulation amount of the object from the device storing information associated with the object via a near field communication (NFC) as the device storing information associated with the object is tagged to the X-ray apparatus.

16. The X-ray apparatus of claim 10, wherein the short range wireless communication comprises at least one of a near field communication (NFC), Bluetooth, and Wi-Fi.

17. The X-ray apparatus of claim 10,
    wherein the first information further comprises second information regarding the object including at least one of an object ID, a name of the object, an age of the object, a gender of the object, and a body weight of the object, and
    wherein the imaging protocol determiner identifies whether the object corresponding to information regarding X-ray accumulation amount transmitted to the X-ray apparatus is identical to the object to be X-rayed, based on the second information and determines the imaging protocol based on the second information, according to a result of the identifying.

* * * * *